(12) United States Patent
Heesch

(10) Patent No.: US 6,679,259 B2
(45) Date of Patent: Jan. 20, 2004

(54) PROCESS FOR CONTROLLING A RESPIRATOR

(75) Inventor: Ralf Heesch, Lübeck (DE)

(73) Assignee: Dräger Medizintechnik GmbH, Lübeck (DE)

( * ) Notice: Subject to any disclaimer, the term of this patent is extended or adjusted under 35 U.S.C. 154(b) by 216 days.

(21) Appl. No.: 09/924,694

(22) Filed: Aug. 8, 2001

(65) Prior Publication Data

US 2002/0023646 A1 Feb. 28, 2002

(30) Foreign Application Priority Data

Aug. 22, 2000 (DE) .......................... 100 41 007

(51) Int. Cl.⁷ ..................... A61M 16/00; A62B 7/04; F16K 31/26
(52) U.S. Cl. ............... 128/204.26; 128/204.18; 128/204.21; 128/203.14; 128/203.12; 128/205.18; 128/910
(58) Field of Search .......... 128/204.26, 204.23, 128/204.22, 204.21, 204.18, 203.14, 203.12, 203.18, 203.25, 205.11, 205.14, 205.24, 205.18, 910

(56) References Cited

U.S. PATENT DOCUMENTS 4,617,637 A * 10/1986 Chu et al. .................... 700/275
4,651,729 A * 3/1987 Rae ........................ 128/203.14
4,702,240 A * 10/1987 Chaoui .................. 128/204.18
5,806,513 A * 9/1998 Tham et al. ........... 128/204.22
6,234,170 B1 * 5/2001 Bergkvist ............... 128/205.18
6,422,237 B1 * 7/2002 Engel et al. ........... 128/204.21

FOREIGN PATENT DOCUMENTS

DE 34 27 182 1/1986
DE 39 00 276 7/1990

* cited by examiner

Primary Examiner—Glenn K. Dawson
Assistant Examiner—Mark Rademacher
(74) Attorney, Agent, or Firm—McGlew and Tuttle, P.C.

(57) ABSTRACT

A process and system are provided for controlling a respirator with a breathing circuit (2), an inspiration branch (10) and an expiration branch (12), in which the gas components needed for the respiration are fed in by a fresh gas metering device (20) via a fresh gas line (9), as a result of which at least the amount of breathing gas consumed can be replenished. A breathing gas delivery unit (1) is provided in the inspiration branch (10) and with a volume flow sensor (13) in the expiration branch (12). The fresh gas utilization of the respirator is improved and the process and system reduces the resistances in the breathing circuit (2) for the patient (3) by the breathing gas delivery unit (1) being returned during the phase of expiration at a speed that depends on the volume flow that is measured by the volume flow sensor (13). A maximum percentage of the breathing gas volume expired via the expiration branch (12) reaches the breathing gas delivery unit (1) and can be displaced from there to the patient (3) via the inspiration branch (10).

9 Claims, 1 Drawing Sheet

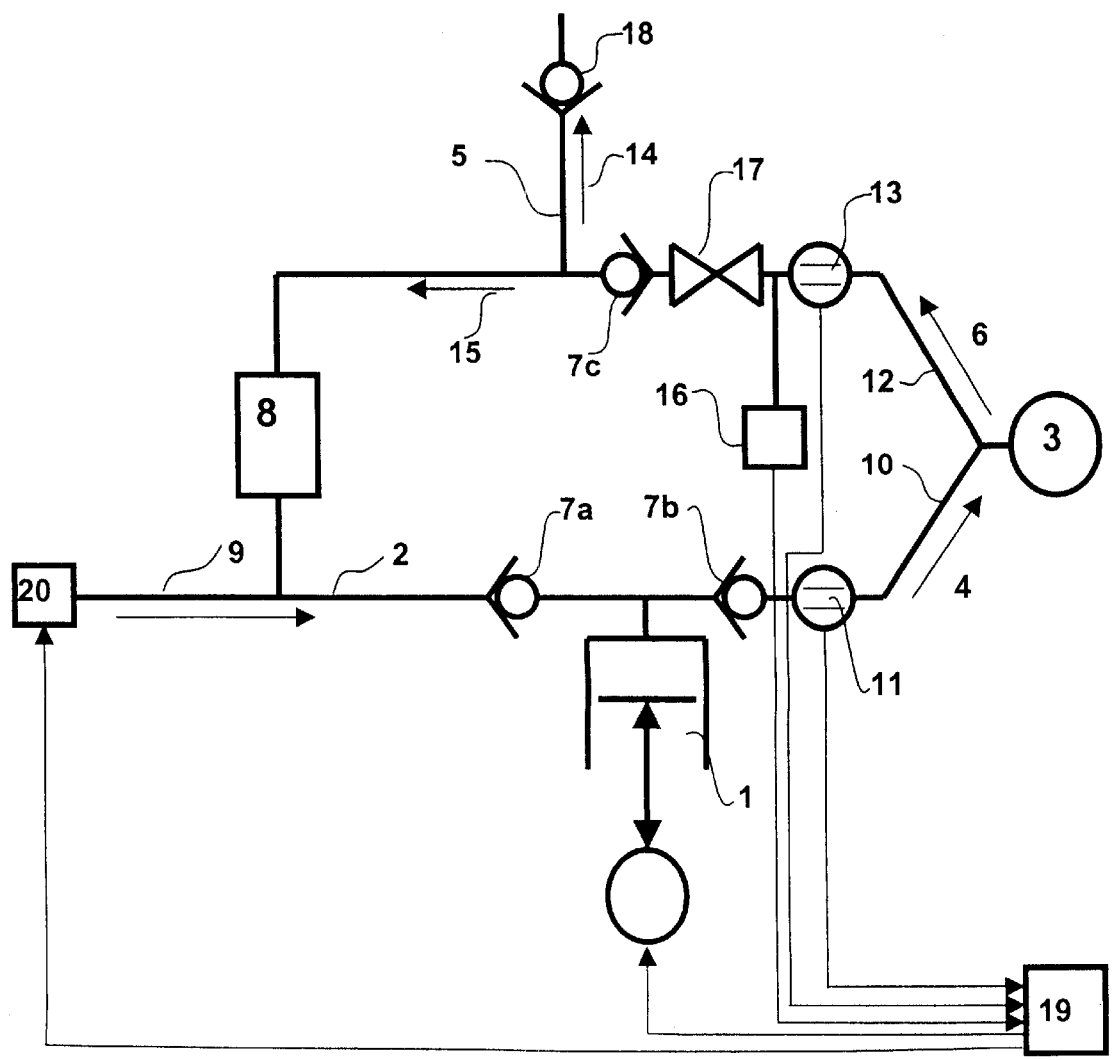

PROCESS FOR CONTROLLING A RESPIRATOR

FIELD OF THE INVENTION

The present invention pertains to a process for controlling a respirator with a breathing circuit, comprising an inspiration branch and an expiration branch, in which the gas components necessary for the respiration are fed via a fresh gas metering means, as a result of which at least the amount of breathing gas consumed can be replenished, with a breathing gas delivery unit in the inspiration branch and with a volume flow sensor in the expiration branch.

BACKGROUND OF THE INVENTION

In a respirator, a breathing gas volume is displaced into the patient during the phase of inspiration. A breathing gas volume expired by the patient is then displaced back into the breathing circuit of the respirator during the phase of expiration. The displacement of the breathing gas volume during the phase of expiration is not supported by the respirator, so that the expiratory resistances occurring in each respirator during the breathing out by the patient must be overcome by the patient himself. This leads to an unintended prolongation of the duration of the phase of expiration compared with the unhindered expiration of the breathing gas volume by the patient.

Furthermore, a fresh gas flow is fed into the breathing circuit of the respirator in order to compensate the breathing gas consumption by the patient and leaks in the respirator. The most effective utilization possible of the fresh gas fed in, which contains generally expensive anesthetic, is desirable in the area of anesthesia in order to save anesthetic, on the one hand, and to protect the environment, on the other hand.

The drawbacks of the state of the art are, on the one hand, expiratory resistances in the breathing circuit of the respirator, against which the patient must work, and which unnaturally prolong the phase of expiration, and, on the other hand, an excessive fresh gas consumption, which entails costs and pollutes the environment in the case of anesthetic gas mixtures.

DE 39 00 276 C2 discloses a respirator of this type, whose metering unit can be uncoupled from the breathing circuit of the respirator itself for fresh gas supply and can be connected to the breathing circuit only when needed during the phase of expiration of the respiration in order to remove the amount of fresh gas from a reservoir filled with fresh gas that must be replaced due to the previous consumption. The fresh gas consumption is thus optimized, even though the drawback of increased design effort, namely, that caused by a metering unit that can be coupled and uncoupled with a fresh gas reservoir, must be accepted for this in return. The problem of the expiratory resistances in the breathing circuit during breathing out by the patient is not dealt with in DE 39 00 276 C2.

DE 34 27 182 C2 contains the description of a process for simulating the lung function and of a lung simulator for carrying out the process. To generate a presettable breathing pattern, which can be described on the basis of the displaced breathing gas volume, this breathing pattern is converted into an electric signal, and the set point and the actual value of the position of a movable wall part of a chamber for displacing the breathing gas volume are compared with one another. The drive device for providing the breathing gas is controlled by this deviation such that it reduces the deviation to a minimum by adjusting the wall part of the chamber. A lung simulator operating according to the operating process can be used to simulate active properties of the lung. The control of the drive device for delivering the breathing gas during the entire respiration cycle, i.e., during the phase of inspiration and the phase of inspiration, as described in DE 34 27 182 C2, is possible, in principle, not only for the simulation of the lung function but also for the actual patient respiration.

SUMMARY AND OBJECTS OF THE INVENTION

The object of the present invention is to provide a process for controlling a respirator of this type, which leads to improved fresh gas utilization in the respirator and to reduced resistances in the breathing circuit of the respirator for the patient respirated therewith.

According to the invention, a process is provided for controlling a respirator with a breathing circuit, comprising an inspiration branch and an expiration branch, in which the gas components needed for the respiration are fed in via a fresh gas metering device. The amount of breathing gas consumed can be replenished with a breathing gas delivery unit in the inspiration branch and with a volume flow sensor in the expiration branch. The breathing gas delivery unit is returned during the phase of expiration at a speed that is directly obtained from the sum of the volume flow that is measured by the volume flow sensor of the volume flow that is fed in via the said fresh gas metering device so that a maximum percentage of the breathing gas volume expired via the expiration branch reaches the breathing gas delivery unit and can be displaced into the inspiration branch during the next phase of inspiration.

The breathing gas delivery unit may be returned during the phase of expiration at a speed that depends, besides on the sum of the volume flows, on the pressure of the breathing gas that is measured by a said pressure sensor, so that when the pressure of the breathing gas drops below a preset minimum pressure $p_{MIN}$ of the breathing gas in the breathing circuit, the return of the breathing gas delivery unit is stopped and is continued only when the minimum pressure $p_{MIN}$ is reached.

The volume of fresh gas which is obtained from the difference between a desired position of the piston and its actual position at the beginning of the particular phase of inspiration may be fed in by the fresh gas metering device via a fresh gas line.

The difference between a desired position of the piston and its actual position at the beginning of the particular phase of inspiration may be displayed to the operator.

The breathing gas delivery unit may be moved forward during the phase of inspiration at a speed that depends on the volume flow that is measured by a said volume flow sensor in the inspiration branch and the pressure of the breathing gas that is measured by the pressure sensor, so that inspiratory airway resistances are compensated and a preset maximum pressure $p_{MAX}$ of the breathing gas in the breathing circuit is not exceeded.

Using the process according to the present invention, it is possible to return a maximum percentage of the breathing gas expired to the patient via the breathing gas delivery unit, so that only a minimum percentage of the expired breathing gas escapes unused via the gaseous anesthetic discharge. At the same time, the minimum end expiratory pressure (also called PEEP for short for Positive End Expiratory Pressure) can be kept as low as possible, which can be considered to be an advantage.

In a preferred embodiment of the process, the pressure of the breathing gas is, moreover, monitored in order not to damage the patient's lungs during respiration with the respirator due to the pressure dropping to below a preset minimum pressure $p_{MIN}$ in the breathing circuit. So much fresh gas is advantageously added that a breathing gas volume set in advance can be administered by the breathing gas delivery unit to the patient via the inspiration branch.

If the corresponding metering of fresh gas does not take place automatically, the missing breathing gas volume can be alternatively displayed to the operator of the respirator, so that he can perform the corresponding metering of fresh gas himself.

The speed control of the breathing gas delivery unit is advantageous not only during the phase of expiration but also during the phase of inspiration because the resistances in the breathing circuit for the patient can thus be avoided during the entire respiration cycle.

One exemplary embodiment of the present invention is shown on the basis of a schematic drawing and will be explained in greater detail below. The figure shows a respirator with the most important components, which can be controlled with the process according to the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only Figure is a schematic view of a respirator operated with the process according to the present invention.

DESCRIPTION OF THE PREFERRED EMBODIMENT

Referring to the drawing in particular, the Figure shows a respirator, which is preferably used in anesthesia, with a fresh gas metering means 20 and a breathing gas delivery unit 1, which may be formed, e.g., by the combination of a cylinder with a piston sliding therein as a volume displacement means. The fresh gas metering means 20 and the breathing gas delivery unit 1 are controlled by an evaluating and control unit 19 and are connected to a breathing circuit 2, which comprises an inspiration branch 10 and an expiration branch 12. The breathing circuit 2 ensures the delivery of the breathing gas to a patient 3 (inspiration arrow 4) during the inspiration and from the patient 3 (expiration arrow 6) to the anesthetic gas discharge 5 or back to the breathing gas delivery unit 1 during the expiration. The circulation of the breathing gas is maintained by the breathing gas delivery unit 1 and is maintained in the circulation direction indicated by the arrows 4, 6 by the nonreturn valves 7a, 7b, 7c. A $CO_2$ absorber 8 is located in the breathing circuit for purifying the breathing gas. The breathing gas that is consumed during a respiration cycle or escapes due to possible leakage can be replenished in the breathing circuit 2 via a fresh gas line 9 by the fresh gas metering means 20, represented by an arrow extending along the fresh gas line 9. The volume flow of the breathing gas in the inspiration branch 10 of the breathing circuit 2 is measured by the volume flow sensor 11, and the volume flow of the breathing gas in the expiration branch 12 of the breathing circuit 2 is measured by the volume flow sensor 13. The values measured by the volume flow sensor 11, the volume flow sensor 13 and a pressure sensor 16 are sent to the evaluating and control unit 19.

The breathing gas expired by the patient 3 via the expiration branch 12 is split during the expiration into two partial flows: A partial flow 14 indicated by a first arrow, which is drawn off through the anesthetic gas discharge, and a partial flow 15 indicated by a second arrow, which is returned into the breathing circuit 2 via the $CO_2$ absorber 8. The splitting of the expired breathing gas into the two partial flows 14 and 15 is due to the resistances present in the breathing system and the pretension of the valve 18 for the anesthetic gas discharge 5. The higher the pretension of the valve 18 for the anesthetic gas discharge 5, the larger the amount of expired breathing gas that is returned into the breathing circuit, but the higher is also the minimum end expiratory pressure $p_{MIN}$ (PEEP).

The goal is to lose as little breathing gas via the anesthetic gas discharge 5 as possible at the lowest possible minimum end expiratory pressure $p_{MIN}$. The total breathing gas expired by the patient 3 shall be ideally returned into the breathing circuit 2.

This is achieved according to the present invention such that the piston of the breathing gas delivery unit 1 is returned during the phase of expiration at a speed that is high enough to return the total amount of the breathing gas volume expired by the patient 3 via the expiration branch 12 together with the new fresh gas fed in via the fresh gas line 9 into the breathing circuit 2 and, mixed with the new fresh gas, it can be drawn into the cylinder of the breathing gas delivery unit 1 and it can be displaced to the patient 3 via the inspiration branch 10 during the next phase of inspiration.

The speed at which the piston of the breathing gas delivery unit 1 is returned is obtained directly from the sum of the volume flow that is measured by the volume flow sensor 13 and the volume flow that is fed in via the fresh gas metering means 20. This process is described as flow-controlled piston return.

In the case of flow-controlled piston return, the pressure of the breathing gas in the breathing circuit 2 must be monitored at the patient 3 for safety reasons in order to prevent the lungs of the patient 3 from being damaged by a vacuum below a preset minimum end expiratory pressure $p_{MIN}$. The pressure of the breathing gas is therefore monitored by the pressure sensor 16. If the pressure being measured by the pressure sensor 16 during the phase of expiration drops below the preset minimum end expiratory pressure $p_{MIN}$, which is set, e.g., by the operator, the return of the piston of the breathing gas delivery unit 1 is stopped and is continued only when the minimum end expiratory pressure $p_{MIN}$ is reached. If the minimum end expiratory pressure $p_{MIN}$ in the breathing circuit 2 is measured at a point remote from the patient 3 rather than near the patient, it may be corrected if necessary by the expiratory airway resistance, multiplied by the expiratory volume flow.

This process is described as flow-controlled, pressure-limited piston return.

If there is a pressure limitation in the case of a flow-controlled, pressure-limited piston return and, as a consequence of this pressure limitation, the piston of the breathing gas delivery unit 1 assumes a position until the end of the phase of expiration that does not permit the complete metering of the breathing gas volume preset for the next phase of inspiration, the fresh gas flow via the fresh gas line 9 is automatically increased by the fresh gas metering means 20, and the necessary increase in the fresh gas flow is derived from the deviation between the necessary position of the piston and the position that the piston has reached at the beginning of the particular phase of inspiration.

As an alternative, the fresh gas flow is not increased automatically, but a display value, which shows recommendations for the operator for the fresh gas control, is formed from the deviation between the necessary position of the piston and the position that the piston has reached.

The difference, which is obtained from a desired position of the piston and its actual position at the beginning of the particular phase of inspiration, is now displayed for the operator.

One advantage of the flow-controlled, pressure-limited piston return of the breathing gas delivery unit 1 is, e.g., the reduction in the expiratory resistance, because the resistance is compensated during the piston return by the absorber 8, the nonreturn valve 7c in the expiration branch 12, a valve 17 for regulating the minimum end expiratory pressure $p_{MIN}$ and the lines located between them in the expiration branch 12. The inspiratory resistance can also be reduced in the same manner, e.g., during spontaneous breathing, by the piston of the breathing gas delivery unit 1 being moved forward on the basis of an evaluation of the volume flow measurements performed by the volume flow sensor 11.

The piston of the breathing gas delivery unit 1 is moved forward during the phase of inspiration at a speed that depends on the volume flow, which is measured by the volume flow sensor 11 in the inspiration branch 10, and on the pressure of the breathing gas, which is measured by the pressure sensor 16, so that inspiratory airway resistances are compensated and a preset maximum pressure $p_{MAX}$ of the breathing gas in the breathing circuit 2 is not exceeded at the same time.

While specific embodiments of the invention have been shown and described in detail to illustrate the application of the principles of the invention, it will be understood that the invention may be embodied otherwise without departing from such principles.

What is claimed is:

1. A process for controlling a respirator with a breathing circuit, the process comprising the steps of:
    providing a respirator with a breathing circuit with an inspiration branch and an expiration branch;
    providing a fresh gas metering device fir feeding gas components needed for the respiration for at least replenishing an amount of breathing gas consumed;
    providing a breathing gas delivery unit in the inspiration branch, the gas delivery unit having a delivery stroke;
    providing a volume flow sensor in the expiration branch; measuring the volume flow with the volume flow sensor to provide a volume flow measurement; and
    returning the breathing gas delivery unit from the delivery stroke position during the phase of expiration at a speed that is directly obtained from the sum of the volume flow measurement and the volume flow fed in via the flesh gas metering device, so that a maximum percentage of the breathing gas volume expired via the expiration branch reaches the breathing gas delivery unit and can be displaced into the inspiration branch during a next phase of inspiration.

2. A process in accordance with claim 1, wherein the breathing gas delivery unit is returned during the phase of expiration at a speed that further depends, in addition to depending on the sum of the volume flows, on the pressure of the breathing gas that is measured by a pressure sensor, so that when the pressure of the breathing gas drops below a preset minimum pressure $p_{MIN}$ of the breathing gas in the breathing circuit, the return of the breathing gas delivery unit is stopped and is continued only when the minimum pressure $p_{MIN}$ is reached.

3. A process in accordance with claim 1, wherein the gas delivery unit is a piston and the volume of fresh gas is obtained from the difference between a desired position of the piston and its actual position at the beginning of the particular phase of inspiration is fed in by the flesh gas metering device via a fresh gas line.

4. A process in accordance with claim 1, wherein the difference between a desired position of the piston and its actual position at the beginning of the particular phase of inspiration is displayed to the operator.

5. A process in accordance with claim 1, wherein the breathing gas delivery unit is moved forward during the phase of inspiration at a speed that depends on the volume flow that is measured by a volume flow sensor in the inspiration branch and the pressure of the breathing gas that is measured by the pressure sensor, so that inspiratory airway resistances are compensated and a preset maximum pressure $p_{MAX}$ of the breathing gas in the breathing circuit is not exceeded.

6. A process for controlling a respirator with a breathing circuit the process comprising the steps of:
    providing a breathing circuit with an inspiration branch and an expiration branch
    feeding gas components needed for the respiration into said breathing circuit via a fresh gas metering device;
    employing a breathing gas delivery unit with a piston device in the inspiration branch to deliver breathing gas with a delivery stroke;
    measuring the volume flow with a volume flow sensor to provide a volume flow measurement; and
    returning the breathing gas delivery unit from a delivery stroke position during the phase of expiration at a speed that is directly obtained from the sum of the volume flow measurement and the volume flow fed in via the fresh gas metering device whereby a maximum percentage of the breathing gas volume expired via the expiration branch reaches the breathing gas delivery unit and can be displaced into the inspiration branch during a next phase of inspiration.

7. A process in accordance with claim 6, wherein the breathing gas delivery unit is returned during the phase of expiration at a speed that further depends, in addition to depending on the sum of the volume flows, on the pressure of the breathing gas that is measured by a pressure sensor, so that when the pressure of the breathing gas drops below a preset minimum pressure $p_{MIN}$ of the breathing gas in the breathing circuit the return of the breathing gas delivery unit is stopped and is continued only when the minimum pressure $p_{MIN}$ is reached.

8. A respirator, comprising:
    a breathing circuit with an inspiration branch and an expiration branch;
    a fresh gas metering device connected to said breathing circuit for feeding gas components needed for the respiration for at least replenishing an amount of breathing gas consumed;
    a breathing gas delivery unit in the inspiration branch with a gas delivery unit piston having a delivery stroke;
    a volume flow sensor in the expiration branch measuring the volume flow with the volume flow sensor to provide a volume flow measurement; and a control unit connected to said volume flow sensor and to said breathing gas delivery unit for returning the breathing gas delivery unit from the delivery stroke position during the phase of expiration at a speed that is directly obtained from the sum of the volume flow measurement and the volume flow fed in via the fresh gas metering device, so that a maximum percentage of the breathing gas volume expired via the expiration branch reaches the breathing gas delivery unit and can be displaced into the inspiration branch during a next phase of inspiration.

9. A respirator in accordance with claim 8, wherein the breathing gas delivery unit is returned during the phase of expiration by command of said control unit at a speed that further depends, in addition to depending on the sum of the volume flows, on the pressure of the breathing gas that is measured by a pressure sensor, so that when the pressure of the breathing gas drops below a preset minimum pressure $p_{MIN}$ of the breathing gas in the breathing circuit the return of the breathing gas delivery unit is stopped and is continued only when the minimum pressure $p_{MIN}$ is reached.

* * * * *